US009186257B2

(12) United States Patent
Geisler et al.

(10) Patent No.: US 9,186,257 B2
(45) Date of Patent: Nov. 17, 2015

(54) BONE PLATE AND FUSION CAGE INTERFACE

(71) Applicant: Rhausler, Inc., San Carlos, CA (US)

(72) Inventors: Fred Geisler, Chicago, IL (US); Terry Johnston, San Carlos, CA (US)

(73) Assignee: RHAUSLER, INC., San Carlos, CA (US)

( * ) Notice: Subject to any disclaimer, the term of this patent is extended or adjusted under 35 U.S.C. 154(b) by 379 days.

(21) Appl. No.: 13/649,545

(22) Filed: Oct. 11, 2012

(65) Prior Publication Data
US 2014/0107785 A1  Apr. 17, 2014

(51) Int. Cl.
*A61F 2/44* (2006.01)
*A61F 2/30* (2006.01)
*A61B 17/70* (2006.01)

(52) U.S. Cl.
CPC ............... *A61F 2/442* (2013.01); *A61F 2/447* (2013.01); *A61B 17/7059* (2013.01); *A61F 2/30965* (2013.01); *A61F 2002/30011* (2013.01); *A61F 2002/30013* (2013.01); *A61F 2002/3092* (2013.01); *A61F 2002/30383* (2013.01); *A61F 2002/30433* (2013.01); *A61F 2002/30517* (2013.01); *A61F 2002/30774* (2013.01); *A61F 2002/30785* (2013.01); *A61F 2002/30879* (2013.01); *A61F 2002/30909* (2013.01); *A61F 2002/30915* (2013.01); *A61F 2002/4475* (2013.01); *A61F 2310/00017* (2013.01);
(Continued)

(58) Field of Classification Search
CPC ....... A61F 2/44; A61F 2/4455; A61F 2/4465; A61F 2/447; A61F 2002/30517; A61B 17/7059; A61B 17/80

USPC .............................................. 623/17.11–17.16
See application file for complete search history.

(56) References Cited

U.S. PATENT DOCUMENTS 6,231,610 B1   5/2001  Geisler
7,815,681 B2 * 10/2010  Ferguson ................... 623/17.16
(Continued)

FOREIGN PATENT DOCUMENTS

WO    2007098288 A2    8/2007
WO    2008154326 A1   12/2008
WO    2010096773 A1    8/2010

OTHER PUBLICATIONS dictionary.com definition of "cage" http://dictionary.reference.com/browse/cage?s=t Nov. 12, 2014.*
(Continued)

*Primary Examiner* — Ellen C Hammond
(74) *Attorney, Agent, or Firm* — Kramer Amado P.C.

(57) ABSTRACT

Various exemplary embodiments relate to a spinal implant for insertion between two adjacent vertebrae, the spinal implant including one or more of the following: a cage comprising: a frame sized to be inserted between the vertebrae, the frame comprising a fastener hole and a cage alignment structure, the cage alignment structure comprising at least one of: a cage groove and a cage ridge; a bone plate comprising a bone plate alignment structure a through hole, wherein the bone plate alignment structure comprises at least one of a bone plate groove and a bone plate ridge, and wherein the bone plate alignment structure and the cage alignment structure are configured to interact with each other to provide an indication when the bone plate is properly aligned with the cage; and a fastener to attach the bone plate to the cage when inserted through the through hole and into the fastener hole.

18 Claims, 17 Drawing Sheets

(52) U.S. Cl.
CPC .......... *A61F2310/00023* (2013.01); *A61F 2310/00029* (2013.01); *A61F 2310/00131* (2013.01); *A61F 2310/00179* (2013.01)

(56) References Cited

U.S. PATENT DOCUMENTS

| | | | |
|---|---|---|---|
| 8,100,975 B2* | 1/2012 | Waugh et al. | 623/17.16 |
| 8,187,329 B2* | 5/2012 | Theofilos | 623/17.11 |
| 8,216,312 B2 | 7/2012 | Gray | |
| 8,425,514 B2* | 4/2013 | Anderson et al. | 606/70 |
| 8,480,747 B2* | 7/2013 | Melkent et al. | 623/17.16 |
| 8,523,947 B2* | 9/2013 | Theofilos | 623/17.16 |
| 8,591,588 B2* | 11/2013 | Fraser et al. | 623/17.16 |
| 8,747,474 B2* | 6/2014 | Ferguson | 623/17.16 |
| 2001/0020185 A1* | 9/2001 | Ray | 623/17.11 |
| 2005/0085913 A1* | 4/2005 | Fraser et al. | 623/17.11 |
| 2005/0124993 A1* | 6/2005 | Chappuis | 606/61 |
| 2005/0177245 A1* | 8/2005 | Leatherbury et al. | 623/23.5 |
| 2006/0247650 A1* | 11/2006 | Yerby et al. | 606/90 |
| 2008/0294262 A1* | 11/2008 | Levieux | 623/17.16 |
| 2008/0300634 A1* | 12/2008 | Gray | 606/280 |
| 2010/0145459 A1 | 6/2010 | McDonough et al. | |
| 2010/0217393 A1* | 8/2010 | Theofilos | 623/17.11 |
| 2011/0160860 A1 | 6/2011 | Johnston et al. | |
| 2014/0039623 A1* | 2/2014 | Iott et al. | 623/17.16 |

OTHER PUBLICATIONS

International Search Report dated Jan. 10, 2014 for PCT /US2013/64216.
"Porous Metal & Texture Technologies: High Quality Metal Components & Assemblies: Tecomet: Wilmington, MA" retrieved Oct. 10, 2012, from http://www.tecomet.com/technologies.html.
"Zimmer Technology Trabecular Metal" retrieved Oct. 10, 2012, from http://www.zimmer.com/ctl?template=CP&op=global&action=1&id=33.

* cited by examiner

BONE PLATE AND FUSION CAGE INTERFACE

CROSS REFERENCE TO RELATED APPLICATIONS

This application is related to co-pending application Ser. No. 13/649,608, "FUSION CAGE IMPLANT WITH LATTICE STRUCTURE," the entire disclosure of which is hereby incorporated by reference for all purposes.

TECHNICAL FIELD

Various exemplary embodiments disclosed herein relate generally to surgical implants.

BACKGROUND

Spinal fusion is a surgical technique by which two or more vertebrae are joined together. This technique is used to treat various conditions such as, for example, spinal deformities, damaged spinal discs, and vertebral fractures. Fusion may be effected by the introduction of new bone tissue between the vertebrae to be joined and the stimulation of the natural bone growth capabilities of the vertebrae themselves. In some procedures, spinal discs and/or vertebrae may be replaced with a spacer, or cage, that maintains a proper distance between vertebrae and provides a structure through which the vertebrae may grow and, eventually, fuse together.

SUMMARY

A brief summary of various exemplary embodiments is presented below. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various exemplary embodiments relate to a spinal implant for insertion between two vertebrae, the spinal implant including: a cage including: a frame sized to be inserted between the two vertebrae, and a lattice structure disposed at least partially within the frame and exposed on at least one side of the frame to permit bone growth into the lattice structure.

Various exemplary embodiments relate to a implant including: a cage including a lattice structure that is exposed on at least one side of the cage such that to permit bone growth into the lattice structure; and a bone plate configured to be attached to the cage and at least one bone. The various structures of the implant such as the cage, and bone plate, may be made of various materials including, for example, stainless steel, titanium, polyether ether ketone (PEEK), and/or tantalum.

Various exemplary embodiments relate to a spinal implant for insertion between two adjacent vertebrae, the spinal implant including: a cage including: a frame sized to be inserted between the two vertebrae and including a fastener hole, a lattice structure disposed within the frame and exposed on a top face and a bottom face of the frame to permit bone growth into the lattice structure, and an inner rim disposed between the lattice structure and a through bore extending between a top face and a bottom face of the cage; a bone plate including a through hole, a first screw hole, and a second screw hole, wherein the first screw hole and the second screw hole are positioned to overlie the two vertebrae, respectively, when the bone plate is attached to the cage and the cage is inserted between the two vertebrae; and a fastener operable to attach the bone plate to the cage when the fastener is inserted through the through hole of the bone plate and into the fastener hole of the frame. In various embodiments, the bone plate may include additional screw holes; for example, up to four threaded holes or holding type structures may be provided to provide fixation and to prevent back-out.

Various embodiments are described wherein the lattice structure is a non-random lattice structure.

Various embodiments are described wherein the non-random lattice structure is a machined, porous, titanium structure.

Various embodiments are described wherein the non-random lattice structure is Trabeculite™ material.

Various embodiments are described wherein the lattice structure is a random lattice structure.

Various embodiments are described wherein the random lattice structure is Trabecular Metal™ material.

Various embodiments are described wherein: the cage further includes a through bore, and the lattice structure is further exposed to the through bore.

Various embodiments are described wherein the cage further includes an inner rim disposed between a portion of the lattice structure and the through bore.

Various embodiments additionally include a bone plate configured for attachment to the cage and to at least one vertebra.

Various embodiments are described wherein the lattice structure contains support material.

Various embodiments are described wherein the support material includes a polymer.

Various embodiments are described wherein the polymer is polyether ether ketone (PEEK).

Various embodiments are described wherein the support material is disposed within a plurality of pores formed by the lattice structure.

Various embodiments are described wherein: the lattice structure includes a channel formed therein; and the support material is disposed within the channel.

Various embodiments are described wherein the lattice structure includes a coating that promotes bone growth.

Various exemplary embodiments relate to a spinal implant for insertion between two vertebrae, the spinal implant including: a cage sized to be inserted between the two vertebrae; and a bone plate configured to be attached to the cage and at least one vertebra, wherein the bone plate includes a bone plate alignment structure configured to interact with the cage to provide an indication when the bone plate is properly aligned with the cage.

Various exemplary embodiments relate to a surgical kit including: a cage sized to be inserted between two vertebrae; a first bone plate configured to be attached to the cage such that the bone plate is oriented at a first angle with respect to the cage; and a second bone plate configured to be attached to the cage such that the bone plate is oriented at a second angle with respect to the cage, wherein the first angle does not equal the second angle.

Various exemplary embodiments relate to a implant including: a cage; and a bone plate configured to be attached to the cage and at least one bone, wherein the bone plate includes a bone plate alignment structure configured to interact with the cage to provide an indication when the bone plate is properly aligned with the cage.

Various exemplary embodiments relate to a spinal implant for insertion between two adjacent vertebrae, the spinal implant including: a cage including: a frame sized to be inserted between the two vertebrae, the frame including a fastener hole and a cage alignment structure, the cage alignment structure including at least one of: a cage groove and a cage ridge, an inner rim surrounding a through bore extending between a top face and a bottom face of the cage; a bone plate including a bone plate alignment structure, a through hole, a first screw hole, and a second screw hole, wherein the first screw hole and the second screw hole are positioned to overlie the two vertebrae, respectively, when the bone plate is attached to the cage and the cage is inserted between the two vertebrae, wherein the bone plate alignment structure includes at least one of a bone plate groove and a bone plate ridge, and wherein the bone plate alignment structure and the cage alignment structure are configured to interact with each other to provide an indication when the bone plate is properly aligned with the cage, the indication including at least one of: the bone plate ridge being seated within the cage groove, and the cage ridge being seated within the bone plate groove; and a fastener operable to attach the bone plate to the cage when the fastener is inserted through the through hole of the bone plate and into the fastener hole of the frame.

Various embodiments are described wherein: the cage further includes a cage alignment structure, and the bone plate alignment structure being configured to interact with the cage includes the bone plate alignment structure being configured to interact with the cage alignment structure.

Various embodiments are described wherein: the bone plate alignment structure includes at least one of: a bone plate groove and a bone plate ridge; the cage alignment structure includes at least one of: a cage groove and a cage ridge; and the indication when the bone plate is properly aligned with the cage includes at least one of: the bone plate ridge being seated within the cage groove, and the cage ridge being seated within the bone plate groove.

Various embodiments are described wherein: the bone plate alignment structure includes a first linear feature and a second linear feature perpendicular to the first linear feature; the first linear feature includes at least one of: a first groove and a first ridge; and the second linear feature includes at least one of: a second groove and a second ridge.

Various embodiments are described wherein the bone plate is configured to attach to the cage such that the bone plate is oriented at a non-zero angle with respect to the cage.

Various embodiments are described wherein the bone plate includes a wedge-shaped foot that contacts the cage.

Various embodiments additionally include a wedge configured to be disposed between the cage and the bone plate.

In various embodiments, the spinal implant may be stackable for multi-level fusion procedures. For example, the bone plate may be shaped such that two adjacent bone plates may tessellate or otherwise fit together or avoid interference with each other when two similar implants are placed in adjacent interveterbral disc spaces.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure or substantially the same or similar function.

DETAILED DESCRIPTION

Figure 1:
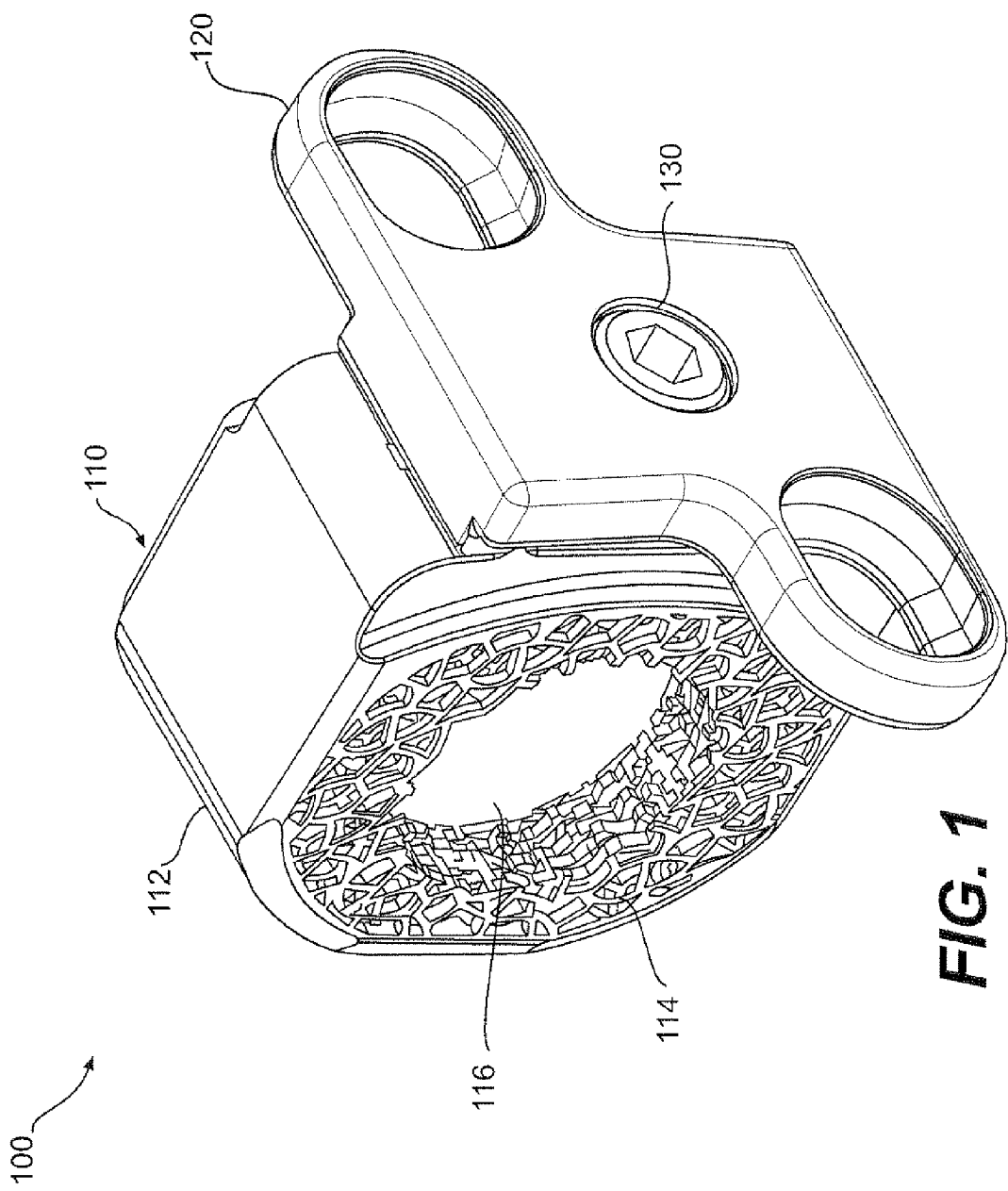
FIG. 1 illustrates a perspective view of an exemplary spinal implant.

FIG. 1 illustrates a perspective view of an exemplary spinal implant 100. The spinal implant 100 includes a cage 110, a bone plate 120, and a fastener 130. The cage 110 and the bone plate 120 may be coupled together by means of the fastener 130.

The cage 110 may be sized to be inserted between two vertebrae. In various embodiments, the cage 110 may be sized for insertion between adjacent vertebrae or may be sized to replace one or more vertebrae and, as such, may constitute a vertebral body replacement. In various embodiments, the cage 110 may be sized for insertion between cervical, thoracic, and/or lumbar vertebrae. The cage 110 may include a frame 112, a lattice structure 114, and an inner rim 116.

The frame 112 may be formed of various materials. In various embodiments, the frame 112 may be formed of a metal such as, for example, titanium, titanium alloy, stainless steel, cobalt-chrome, or tantalum. Alternatively, the frame 112 may be formed of a ceramic or a plastic, such as polyether ether ketone (PEEK) or carbon fiber. The frame 112 may define a perimeter of the cage and may, at least partially, contain the lattice structure 114 and inner rim 116.

The lattice structure 114 may be formed of a metal such as, for example, titanium, titanium alloy, stainless steel, cobalt-chrome, or tantalum. Alternatively, the lattice structure 114 may be formed of a ceramic or a plastic, such as polyether ether ketone (PEEK) or carbon fiber. The lattice structure 114 may include a lattice of material onto which bone may root. In other words, the lattice structure 114 provides a plurality of small pores into which bone may grow, thereby fixing the implant in place and providing a scaffold through which vertebrae may grow toward each other.

In various embodiments, the lattice structure 114 may be a non-random lattice structure such as, for example, Trabeculite™ material. or another machined, porous, titanium structure. As such, the lattice structure may include a plurality of layers, each layer including a non-random lattice of material. In various alternative embodiments, the lattice structure 114 may instead be a random lattice structure such as, for example, Trabecular Metal™ material.

The lattice structure 114 may be exposed by the frame 112 on at least one side of the cage 110. More preferably, the lattice structure 114 is exposed on both the top and bottom sides of the cage 110. Such exposure may allow the lattice structure 114 to directly contact vertebrae or other bone that is desired to anchor into the cage 110. In various embodiments, bone growth may be further facilitated through use of a coating on the lattice structure 114 and/or other features of the implant 100. For example, the lattice structure 114 may be provided with an osteo-integration coating or may be roughened to provide additional surface area that contacts bone.

In various embodiments, such as that illustrated in FIG. 1, the cage 110 may include a through bore extending from the top face of the cage to the bottom face. In such embodiments, the cage 110 may further include an inner rim 116 disposed between the lattice structure 114 and the through bore. The inner rim 116 may be formed of a metal such as, for example, titanium, titanium alloy, stainless steel, cobalt-chrome, or tantalum. Alternatively, the inner rim 116 may be formed of a ceramic or a plastic, such as polyether ether ketone (PEEK) or carbon fiber. In various alternative embodiments, the cage 110 may not include such a through bore.

The inner rim 116 may not extend entirely from the top face to the bottom face, as is illustrated. In such embodiments, the lattice structure 114 may be partially exposed to the through bore. In various alternative embodiments, such as that which will be described in greater detail below with respect to FIG. 16, the inner rim 116 may extend from the top face to the bottom face, thereby leaving the lattice structure 114 mostly or entirely unexposed to the through bore.

The fastener 130 may be formed of various materials. In various embodiments, the fastener 130 may be formed of a metal such as, for example, titanium, titanium alloy, stainless steel, cobalt-chrome, or tantalum. Alternatively, the fastener 130 may be formed of a ceramic or a plastic, such as polyether ether ketone (PEEK) or carbon fiber.

In various embodiments, the fastener 130 may have a shaft and an enlarged head. The shaft may be threaded. In various alternative embodiments, such as those wherein the screw is formed from bio-absorbable material, the shaft may be unthreaded because the bio-absorbable material may swell in the presence of fluid to achieve sufficient fixation.

Figure 2:
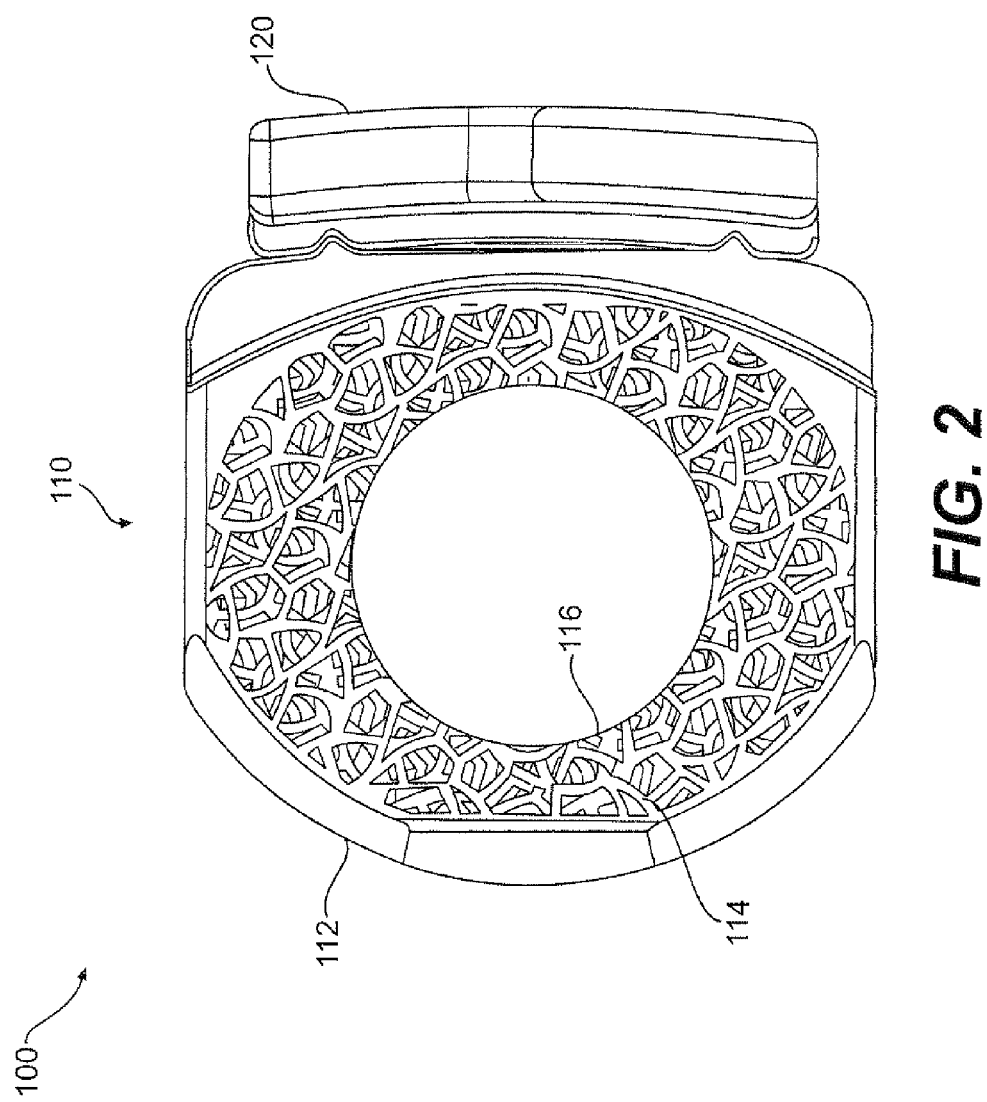
FIG. 2 illustrates a top view of the exemplary spinal implant.
Figure 3:
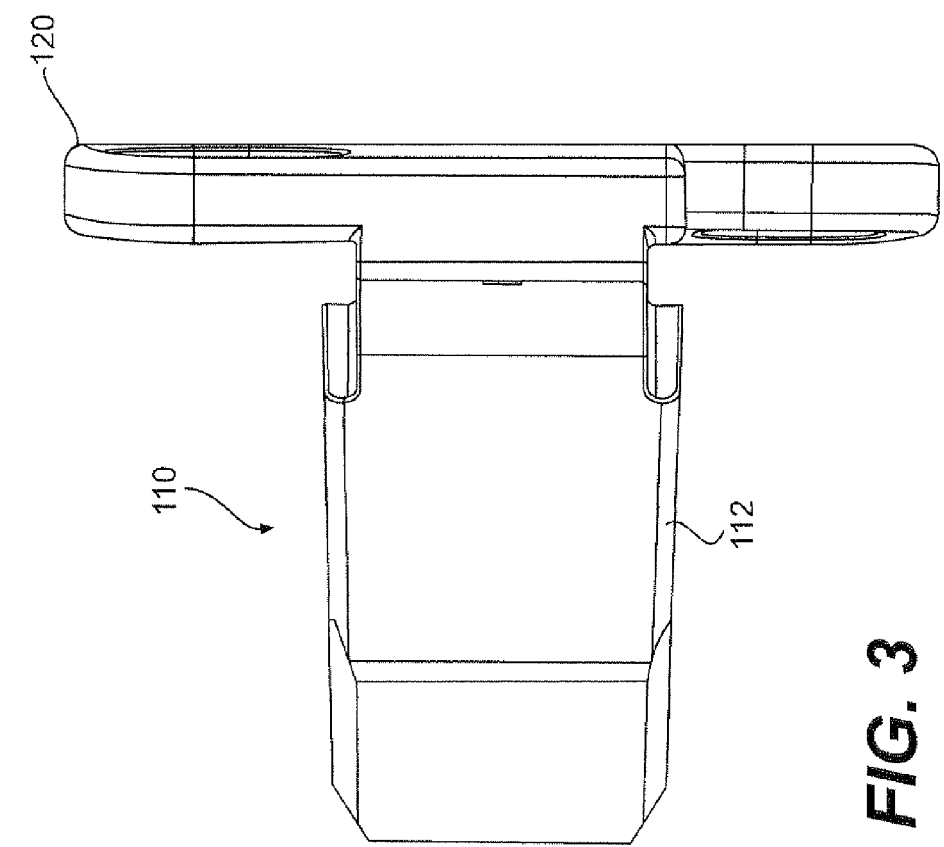
FIG. 3 illustrates a side view of the exemplary spinal implant.

FIGS. 2 and 3 illustrate a top view and side view of the exemplary implant 100, respectively. As can be seen more clearly in FIG. 2, the exemplary lattice structure 114 illustrated is a non-random lattice structure. The lattice structure 114 includes multiple stacked layers, each of which includes a lattice of material. As illustrated in FIG. 3, the lattice structure (not shown) may or may not be exposed on all sides of the cage 110.

Figure 4:
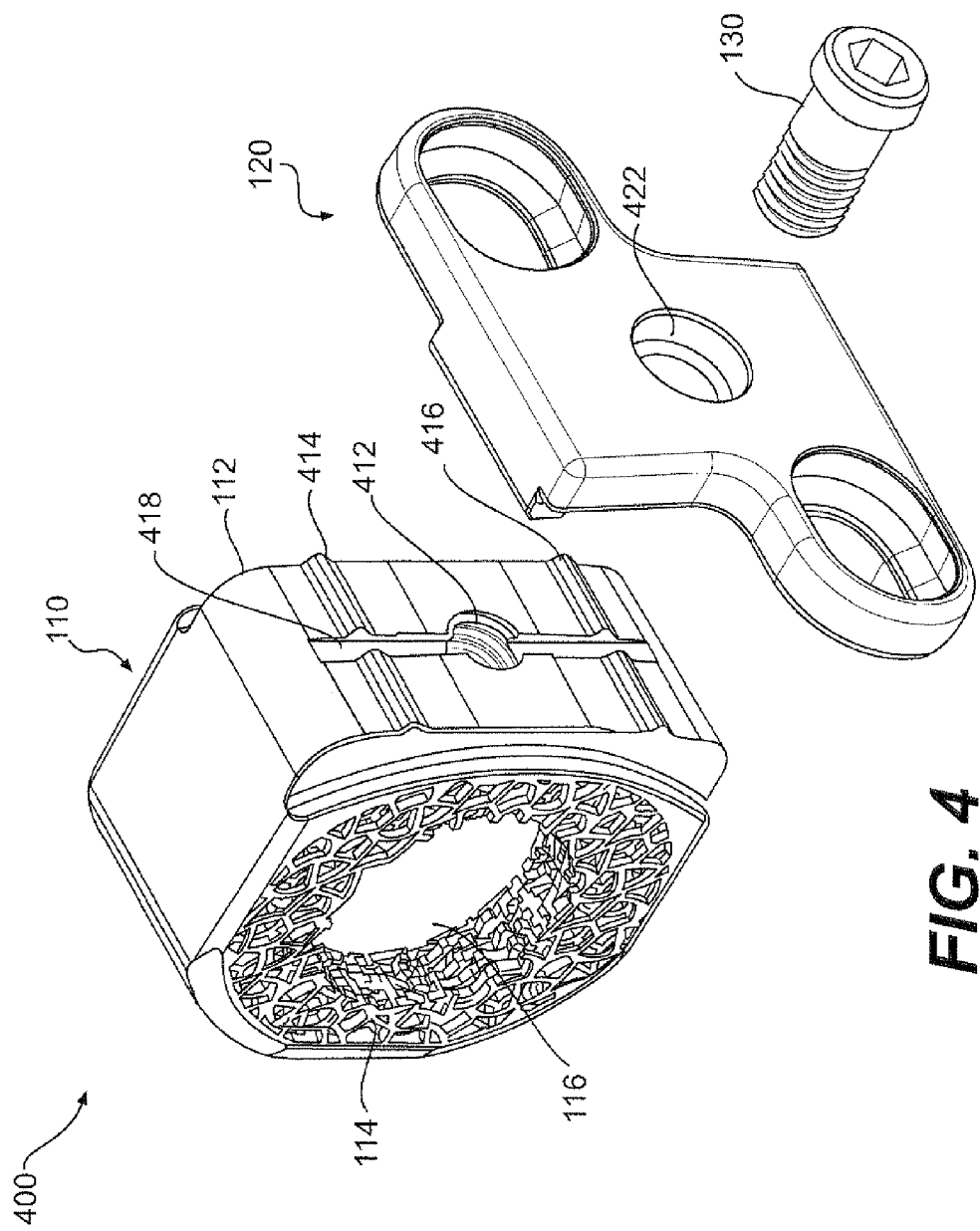
FIG. 4 illustrates a perspective exploded view of the exemplary spinal implant.

FIG. 4 illustrates an exploded view 400 of the exemplary implant 100. As can be seen in FIG. 4, the cage 110 may further include a fastener hole 412, and three linear features 414, 416, 418 that cooperate to form a cage alignment structure. The bone plate 422 may further include a through-hole 422.

The fastener hole 412 and the through-hole 422 may be used in conjunction with the fastener 130 to attach the bone plate 120 to the cage 110. As such, the through-hole 422 may be sized to allow the shaft of the fastener 130 to pass through, but to prevent the head of the fastener 130 from passing. The fastener hole 412 may be sized to receive and engage the shaft of the fastener 130. In those embodiments where the shaft of the fastener 130 is threaded, the fastener hole 412 may be complementarily threaded, so as to engage the screw. In alternative embodiments wherein the shaft of the fastener 130 is not threaded, the fastener hole 412 may be sized to provide a transition or force fit between the shaft of the fastener 130 and the fastener hole 412, when the shaft of the fastener 130 is in either an unexpanded or an expanded (such as in the case of a bio-absorbable material screw) configuration. In various embodiments, the cage 110 may be used without the bone plate 120 or fastener 130. In such embodiments, the fastener hole 412 may or may not be present.

The three linear features 414, 416, 418 may include two parallel ridges 414, 416 and a groove 418 that intersects the ridges 414, 416. Together, the three linear features 414, 416, 418 may form a cage alignment feature that serves to ensure, or otherwise provide an indication as to, proper seating of the bone plate 120 on the front face of the cage 110. In various embodiments, the bone plate 120 may include a complementary bone plate alignment feature (not shown) that engages the cage alignment feature when the bone plate 120 is properly aligned with the cage 110. It will be appreciated that various alternative arrangements of grooves, ridges, and other features suitable for facilitating proper alignment. For example, fewer or additional grooves or ridges may be provided; groove 418 may instead be a third ridge; ridge 414 may intersect groove 418 at an oblique angle; or ridge 414 may instead be an l- or t-shaped channel, an l- or t-shaped prominence, a bump, a dimple, or another structure suitable for engaging a complementary structure.

Figure 5:
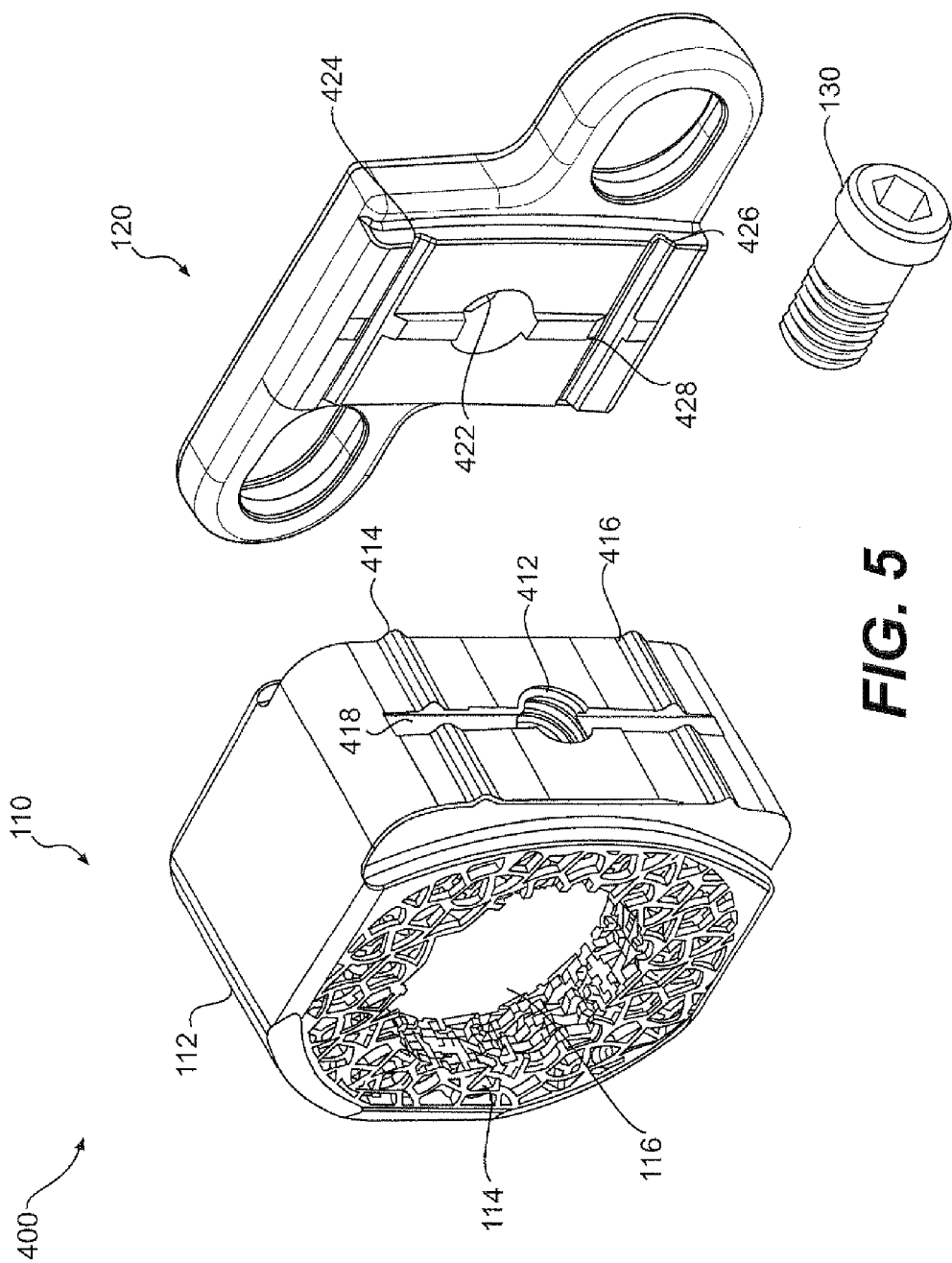
FIG. 5 illustrates another perspective exploded view of the exemplary spinal implant.

FIG. 5 illustrates another exploded view 400 of the exemplary implant 100. In FIG. 5, the bone plate 120 is rotated 90 degrees such that the rear face is visible. As shown, the rear face of the bone plate 120 may include three linear features 424, 426, 428 that together constitute a bone plate alignment feature. The bone plate 120 may include two parallel grooves 424, 426 intersected by a ridge 428. The bone plate alignment feature may engage the cage alignment feature such that ridges 414, 416 are received in grooves 424, 426 respectively, while ridge 428 is received in groove 418. In this manner, the proper seating of the various grooves within corresponding ridges may provide a surgeon with an indication that the bone plate 120 is properly aligned with the cage 110 such that the bone plate may be affixed to the plate and/or adjacent bone.

Figure 7:
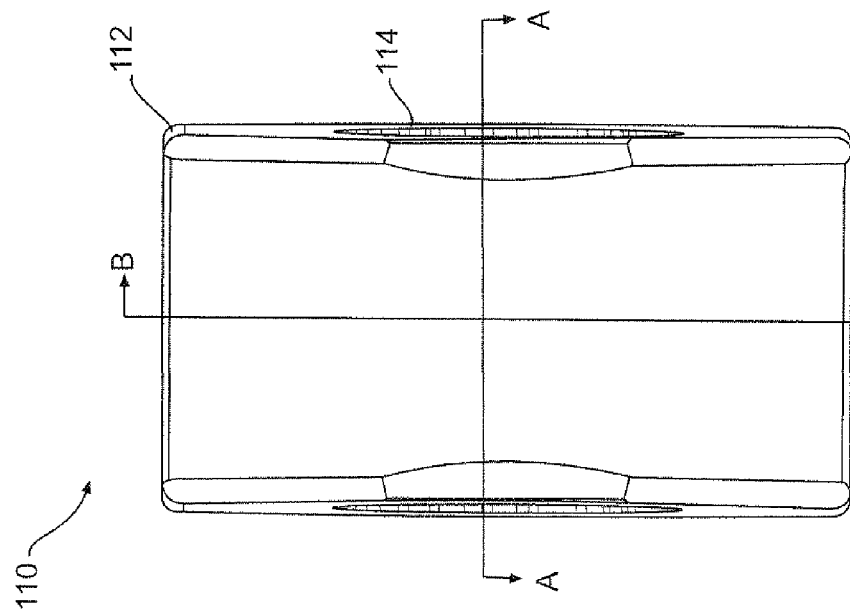
FIG. 7 illustrates a rear view of the exemplary cage.
Figure 6:
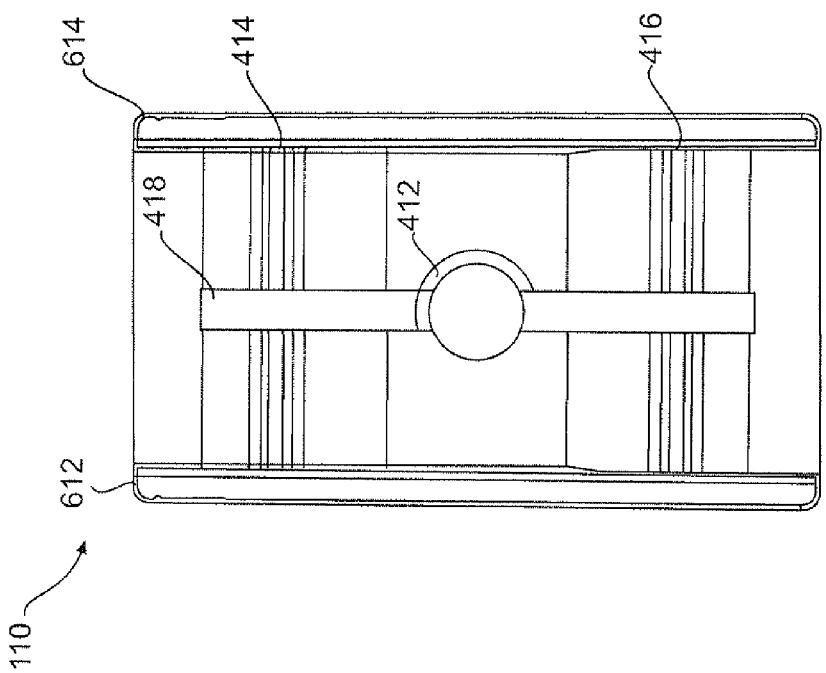
FIG. 6 illustrates a front view of an exemplary cage.

FIG. 6 illustrates a front view of the exemplary cage 110, while FIG. 7 illustrates a rear view of the exemplary cage 110. As can be seen in FIG. 6, the cage 110 further includes a pair of recesses 612, 614. The recesses 612, 614 may provide a recess for the cortical margin of the vertebra; the cortical margin may rest in the recesses 612, 614, while the remainder of the cage 110, including the exposed lattice structure, extends further into the bone. Further, as can be seen in FIGS. 3 and 7, the cage 110 may taper toward the rear end thereof.

Figure 8:
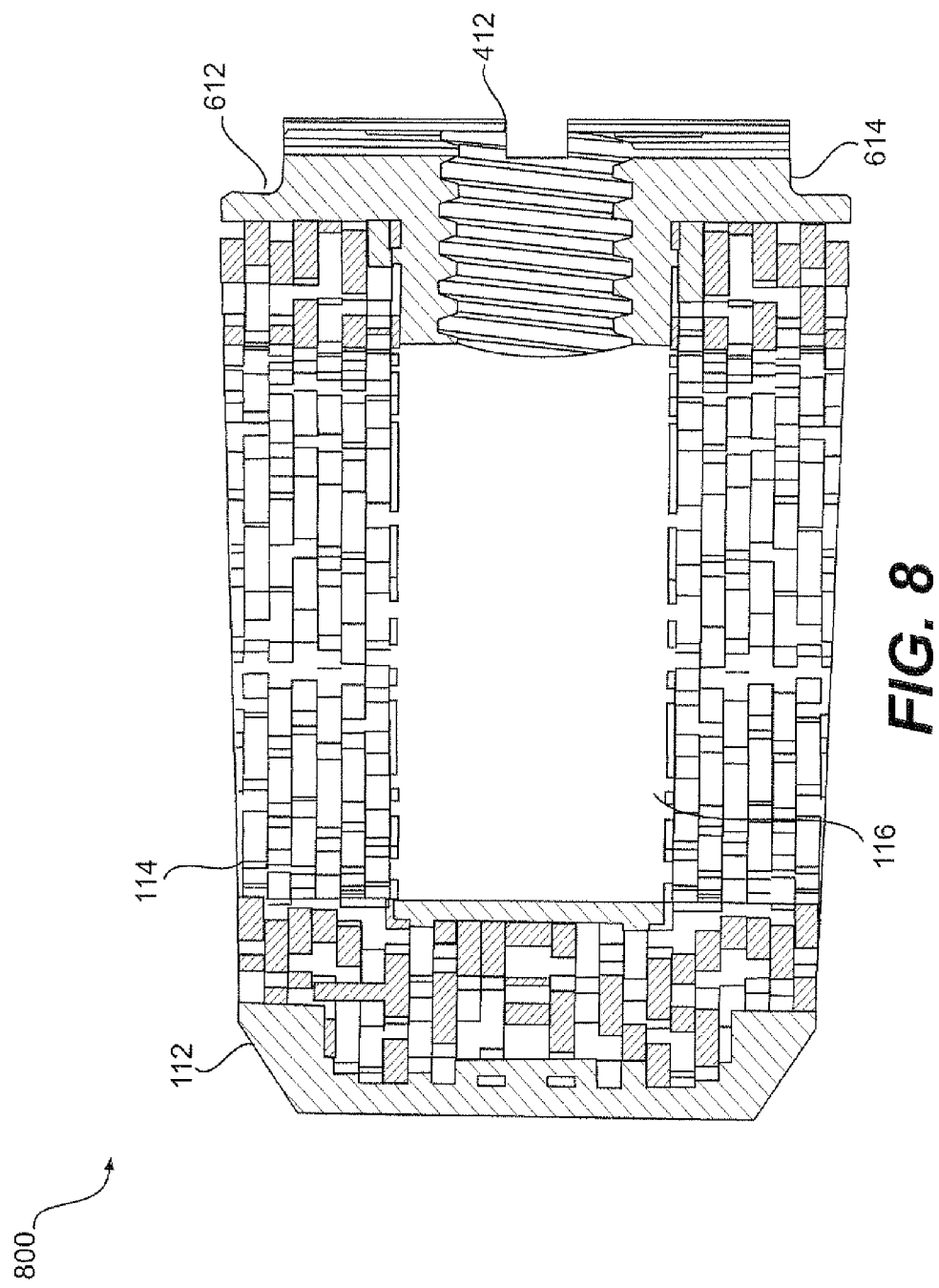
FIG. 8 illustrates a side view cross section of the exemplary cage.

FIG. 8 illustrates a cross section 800 of the exemplary cage 110 taken across line A-A of FIG. 7. As can be seen in the cross section 800, the lattice structure 114 extends from the top face to the bottom face. The lattice structure 114 may include numerous pores into which bone may grow. In various embodiments, the lattice structure may be reinforced using support material. The support material may be a polymer, such as polyether ether ketone (PEEK). Additional materials that may be used as support material will be apparent. In various embodiments, the support material may be received within channels cut or otherwise formed into the lattice structure 114 or the support material may be disposed within the existing pores of the lattice structure 114. Further, the support material may be inserted into the lattice structure in any way such as, for example, press-fitting or injection-molding.

Figure 9:
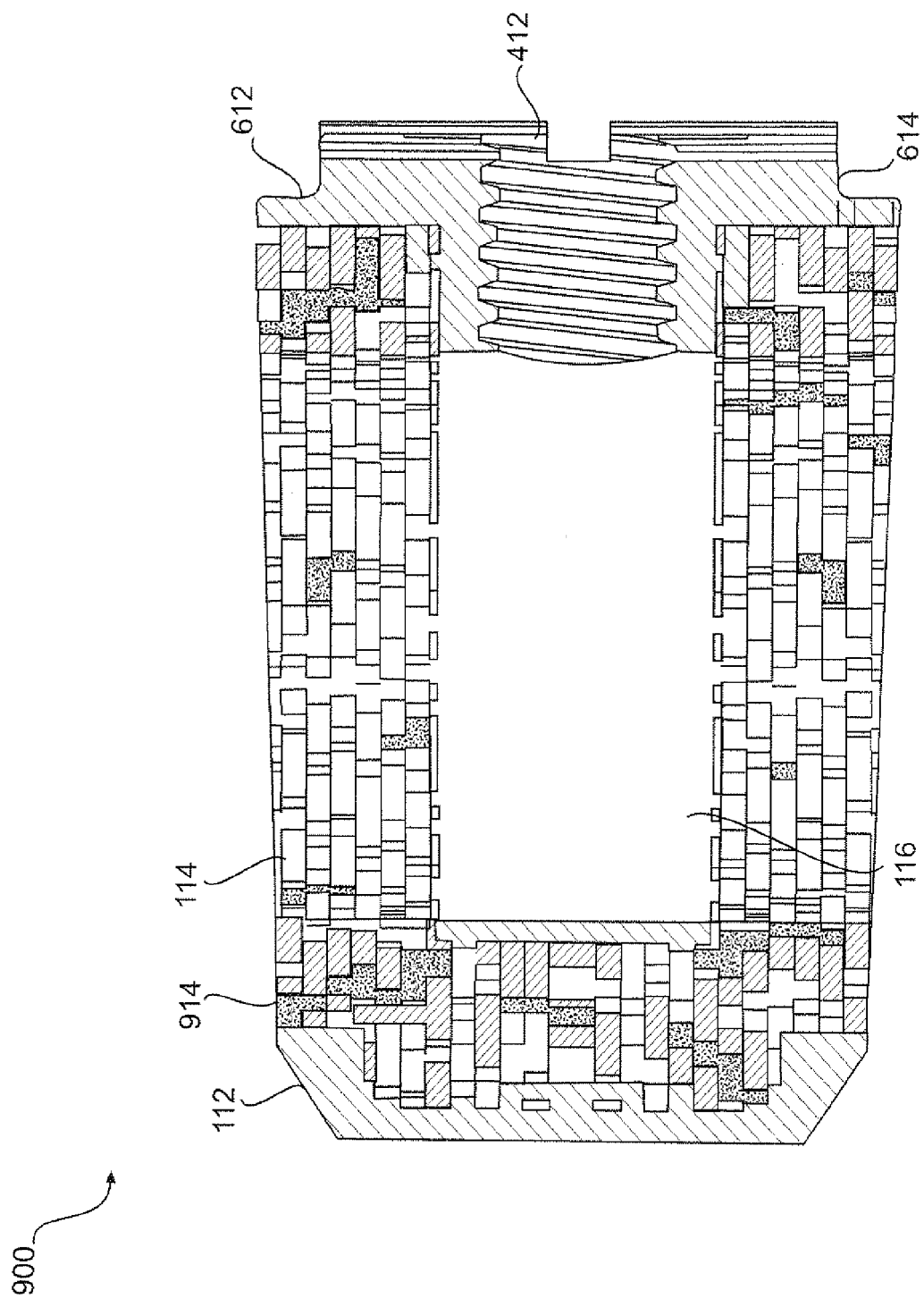
FIG. 9 illustrates a side view cross section of the exemplary cage including support material injected into the lattice structure.

FIG. 9 illustrates another cross section 900 of the exemplary cage 110 taken across line A-A of FIG. 7, after support material 914 (shown in black) has been injected into the lattice structure 114. According to the embodiment of FIG. 7, the support material 914 may be spot injected at a number of selected locations on the surface of the lattice structure 114. As can be seen, the injected support material 914 may fill some of the pores of the lattice structure 114 such that bone may not grow into the filled pores as easily as unfilled pores. The strength of the support material 914, however, may add sufficient strength to the lattice structure 114 so as to resist forces arising from normal spine movement that would work to crush or shear the lattice structure 114.

Figure 10:
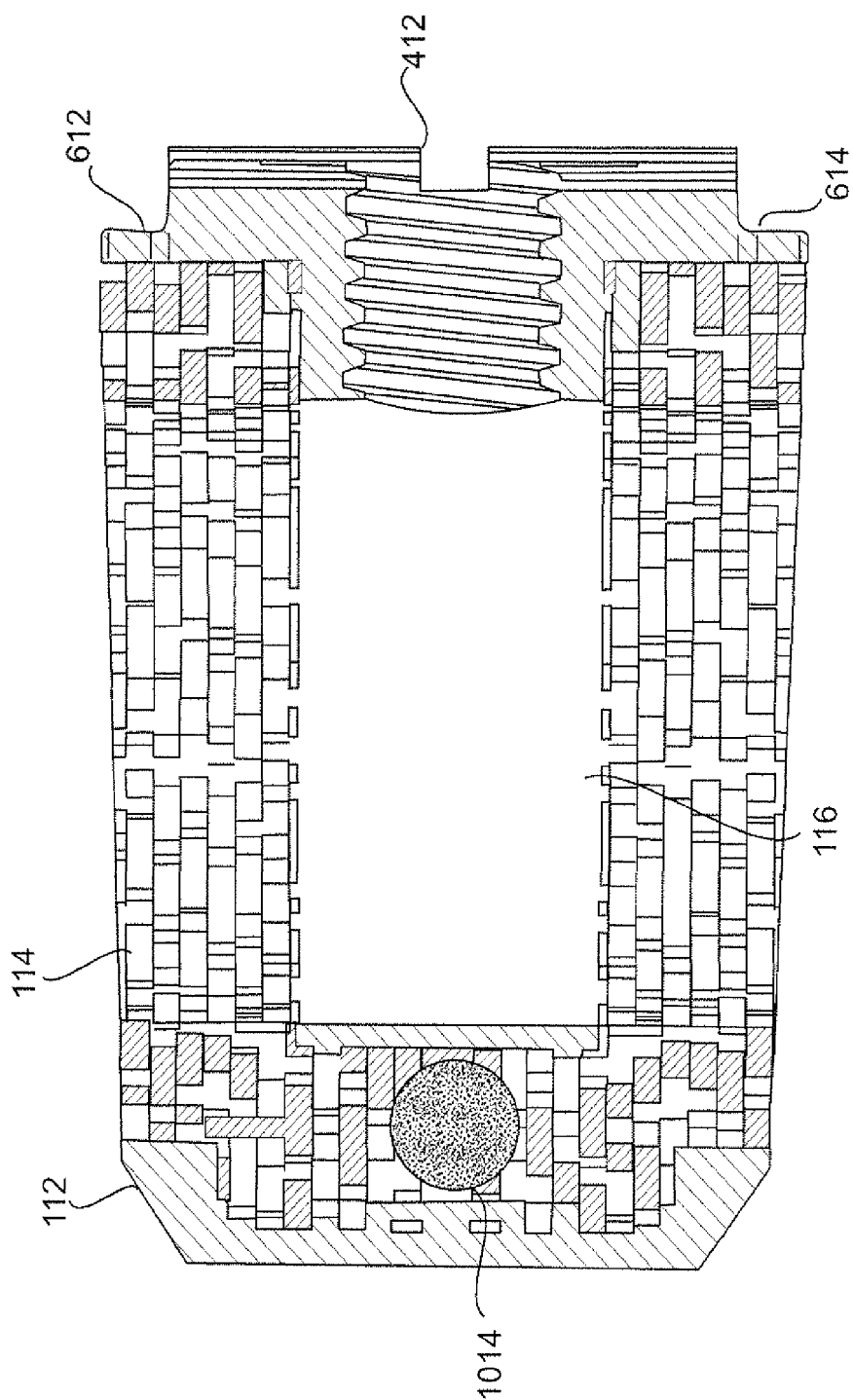
FIG. 10 illustrates a side view cross section of the exemplary cage including support material disposed within a channel formed in the lattice structure.

FIG. 10 illustrates a cross section of an alternative embodiment of the exemplary cage 110 wherein one or more channels may be cut or otherwise formed into the lattice structure 114 for receiving support material. As shown, a circular channel 1014 may be formed into the lattice structure and filled with support material, such as PEEK. The channel 1014 may be linear and extend from one side of the cage to the other, or the channel 1014 may be fully or partially circular, curving around, and substantially concentric with, the through bore and inner rim 116. The channel may 1014 may be in communication with the surrounding lattice structure 114 or may be separated from the lattice structure by a retaining structure such as, for example, a solid wall made of titanium. It will be appreciated that various alternative channels may be formed in the lattice structure 114. An alternative channel may have a cross section other than a circle such as, for example, a diamond, a square, a rectangle, an oval, a crescent, or a half-circle cross section. As another example, an alternative channel may extend from top to bottom, or from front to back, with respect to the cage. An alternative channel may also be in communication with the inner bore of the cage, such a channel extending through the inner rim 116, and/or may be otherwise accessible from outside (prior to being filled with support material), such as a channel extending through the frame 112. Further, an alternative channel may be linear and formed at a non-parallel and/or non-perpendicular angle with respect to one or more faces of the cage. Various other modifications for a channel suitable for receiving support material will be apparent.

Figure 17:
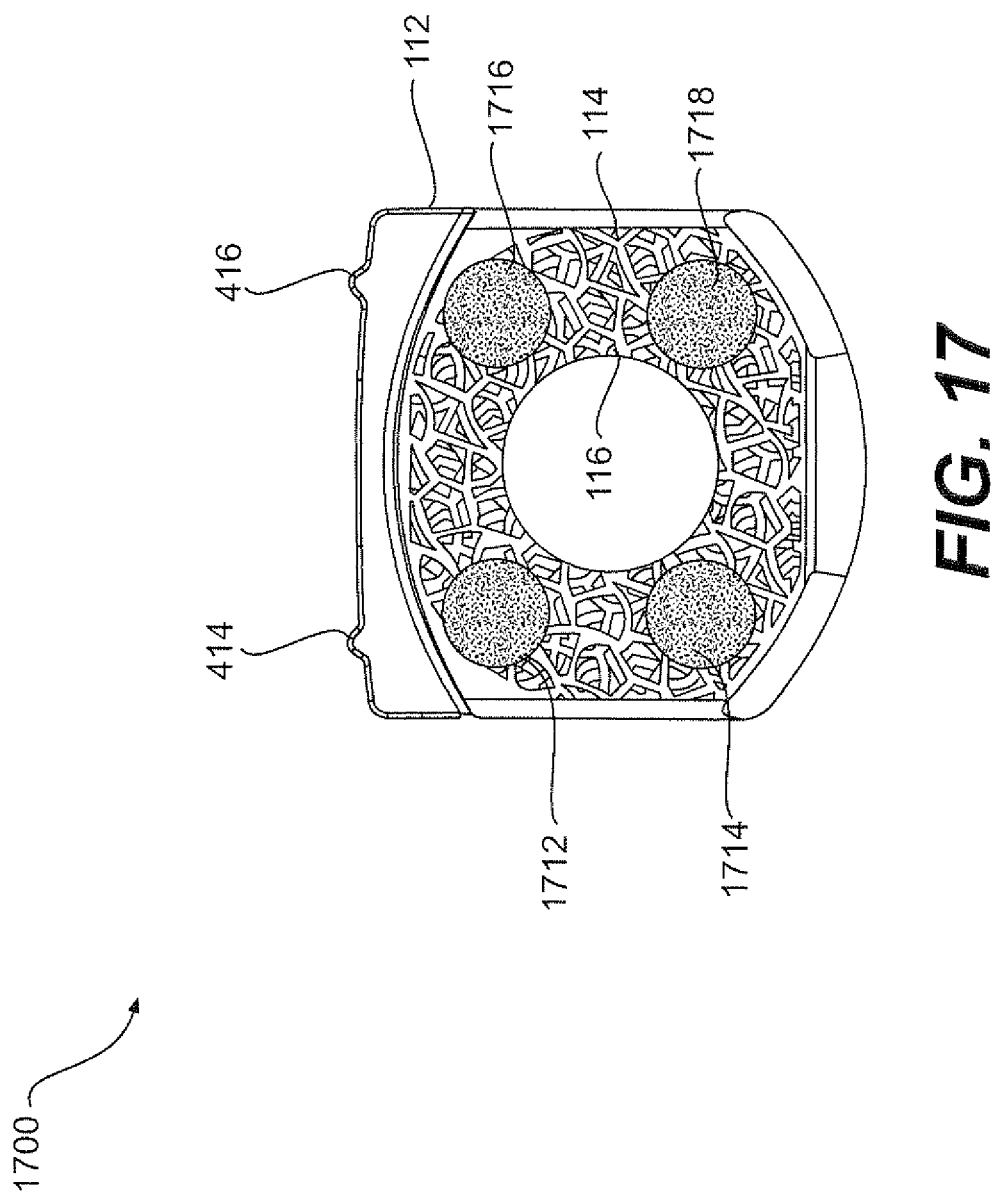
FIG. 17 illustrates a top view of an alternative cage including channels for receiving support material.

FIG. 17 illustrates a top view of an alternative cage 1700 including channels 1712, 1714, 1716, 1718 for receiving support material. As explained above with respect to FIG. 10, channels 1712, 1714, 1716, 1718 may be formed to extend from the top face to the bottom face of the cage 1700. In various alternative embodiments, the channels 1712, 1714, 1716, 1718 may not extend all the way through these top and bottom faces and, instead, leave at least one layer of lattice structure 114 between the channels 1712, 1714, 1716, 1718 and the outer surface of the cage 1700. The channels 1712, 1714, 1716, 1718 may be in communication with the surrounding lattice structure 114 or may be surrounded by a retaining structure such as, for example, a solid wall made of titanium. Support material, such as PEEK, may be injection-molded or press-fit into the channels 1712, 1714, 1716, 1718 to provide the desired support for the cage 1700.

In various embodiments, such as those wherein the channels 1712, 1714, 1716, 1718 do not extend all the way through the top and bottom faces of the cage 1700, the cage 1700 may be formed as two separate pieces, such as a top half and a bottom half. In such embodiments, pre-cut rods of support material may be pressed into the channels 1712, 1714, 1716, 1718 through the openings disposed at what will be an interior portion of the cage 1700 after assembly. Thereafter, the two pieces of the cage 1700 may be pressed together around the rods of support material to form a single cage 1700 including support material.

Figure 18:
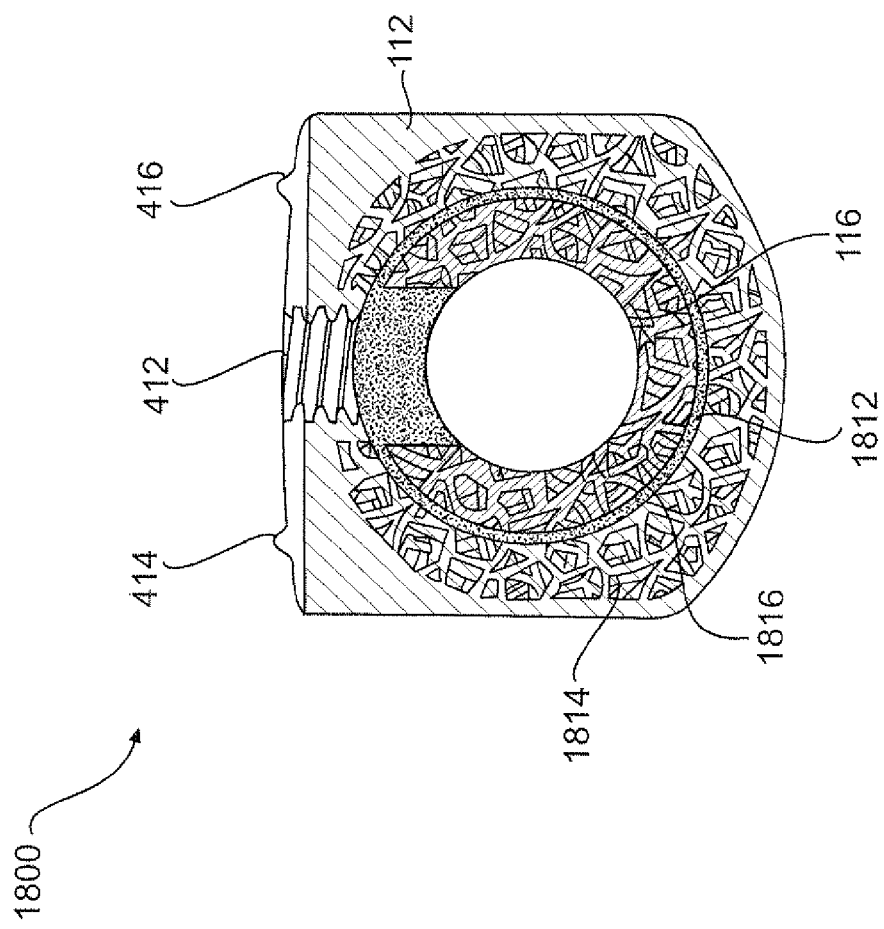
FIG. 18 illustrates an exemplary cross section of a cage including a retaining structure for support material.

FIG. 18 illustrates an exemplary cross section 1800 of a cage including a retaining structure 1812 for support material. The cross section 1800 may be taken along line B-B of FIG. 7. The retaining structure 1812 may be, for example, a solid wall of titanium or other metal. In this embodiment, the cage frame 112 may be formed of PEEK. As can be seen, the retaining structure 1812 forms a circle through the lattice structure, dividing the lattice structure at this cross section into two separate lattice structures 1814, 1816. By dividing the lattice structure into multiple lattice structures 1814, 1816, the cage 1800 is able to receive support material into one such lattice structure 1814, 1816 while keeping the remaining lattice structures 1814, 1816 free from the support material such that bone may grow into the lattice structure. For example, the lattice structure 1814 may be filled with support material while the pores of the lattice structure 1816 may be substantially free from support material.

Figure 19:
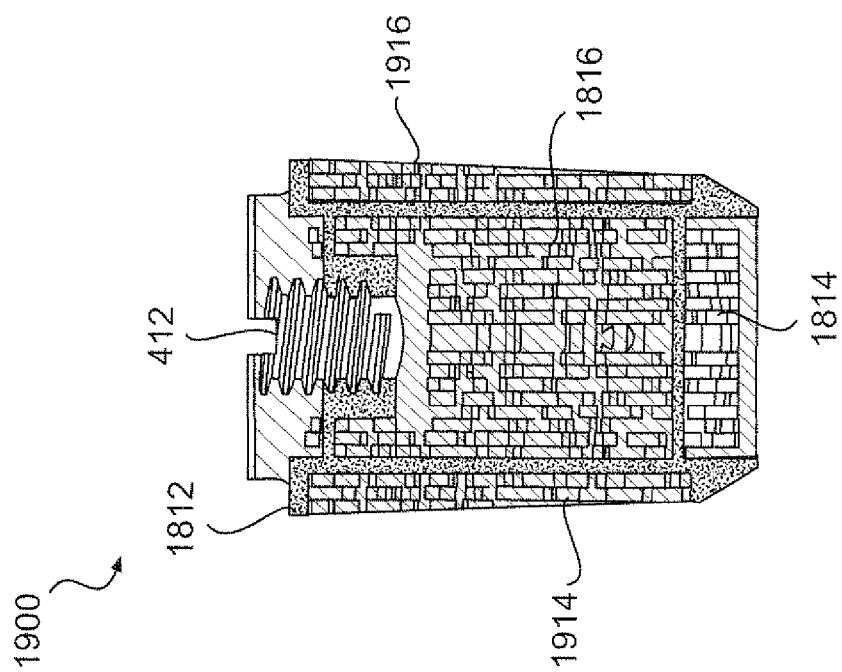
FIG. 19 illustrates another exemplary cross section of the cage including the retaining structure for support material.

FIG. 19 illustrates another exemplary cross section 1900 of the cage including the retaining structure 1812 for support material. As can be seen in this cross section 1900 taken along line A-A of FIG. 7, the retaining structure 1812 may take on a more complex shape than a substantial circle or cylinder. As shown, the retaining structure 1812 may form a larger ring near the top and bottom faces of the cage. At the transitions between the larger outer rings and the smaller inner ring, the retaining structure 1812 may form a shelf and thereby divide the lattice structure into four separate lattice structures 1814, 1816, 1914, 1916. Lattice structures 1814, 1816 may refer to the two lattice structures described with regard to FIG. 18. The two additional lattice structures 1914, 1916 may be disposed near the top and bottom faces, respectively. As described above, any combination of the four lattice structures 1814, 1816, 1914, 1916 may be filled with support material. For example, only lattice structure 1814 may be filled with support material, while lattice structures 1816, 1914, 1916 may be free for bony ingrowth. The outer lattice structures 1914, 1916 may thus provide the entire, or a substantial portion of, the surface area of the undivided lattice structure for bony ingrowth.

Construction of the implant 100 may be performed, at least in part, using 3D printing technology. For example, the cage 110 may be constructed layer-by-layer, bottom-to-top, from titanium such that the frame 112, lattice structure 114, and inner rim 116 are integrally connected. In various embodiments, the cage 110 may be formed as a single piece, or as multiple pieces that are to be subsequently attached to each other. Thereafter, the groove 418 may be cut into the front face of the cage 110 and threads may be cut into the fastener hole 412. PEEK or other support material may then be injected or pressed into one or more pores of the lattice structure 114 or a channel 1014, if present.

FIGS. 11-14 illustrate various views of the bone plate 120. As previously explained, the bone plate 120 may be aligned with respect to the cage 110 using the linear features 424, 426, 428 and subsequently attached to the cage 110 by inserting the fastener 130 through the through hole 422. The linear features 424, 426, 428 may be formed on a foot 1220 of the bone plate 120. The foot 1220 may include the face of the bone plate 120 that contacts the front of the cage 110 and may space the remainder of the bone plate 120 away from the cage 110, such that the bone plate 120 may be disposed outside of the spinal column when the implant 100 is fixed in the patient. The bone plate 120 may additionally include one or more screw holes 1122, 1124 positioned and sized to receive a bone screw (not shown) that is subsequently attached to a vertebra or other bone. In various embodiments, the bone screws and screw holes may be operable to provide fixed, semi-constrained, and/or dynamic fixation.

Figure 11:
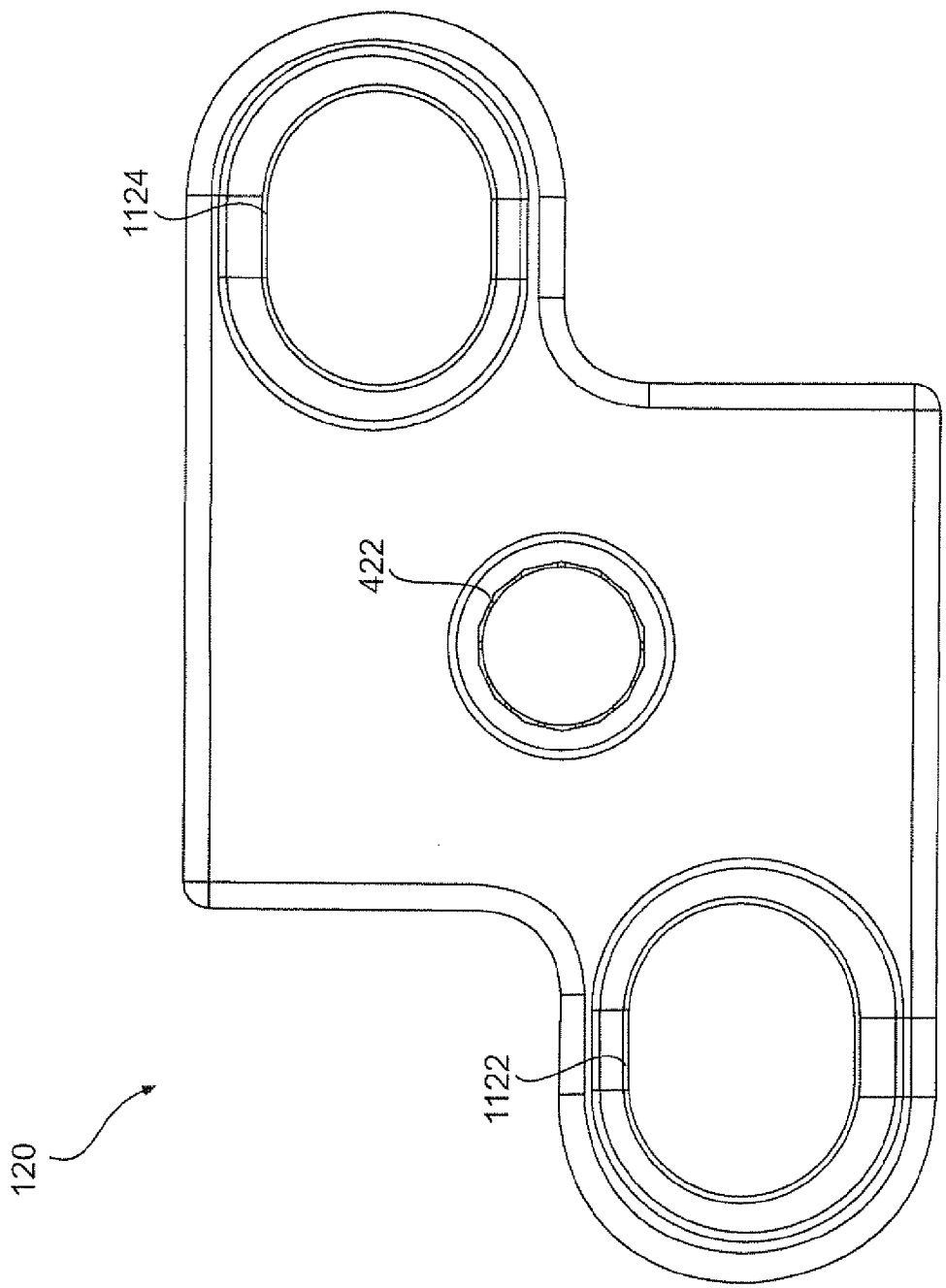
FIG. 11 illustrates a front view of an exemplary bone plate.
Figure 12:
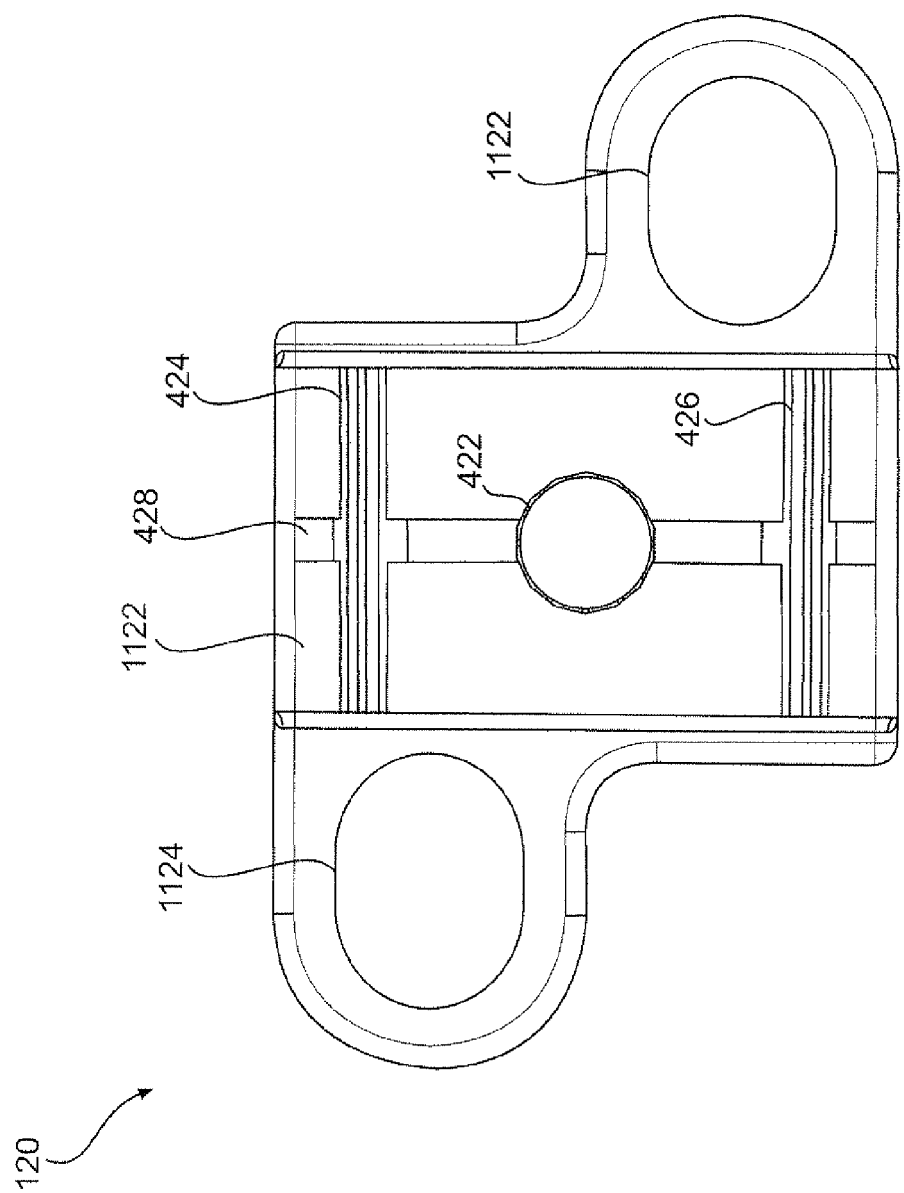
FIG. 12 illustrates a rear view of the exemplary bone plate.
Figure 13:
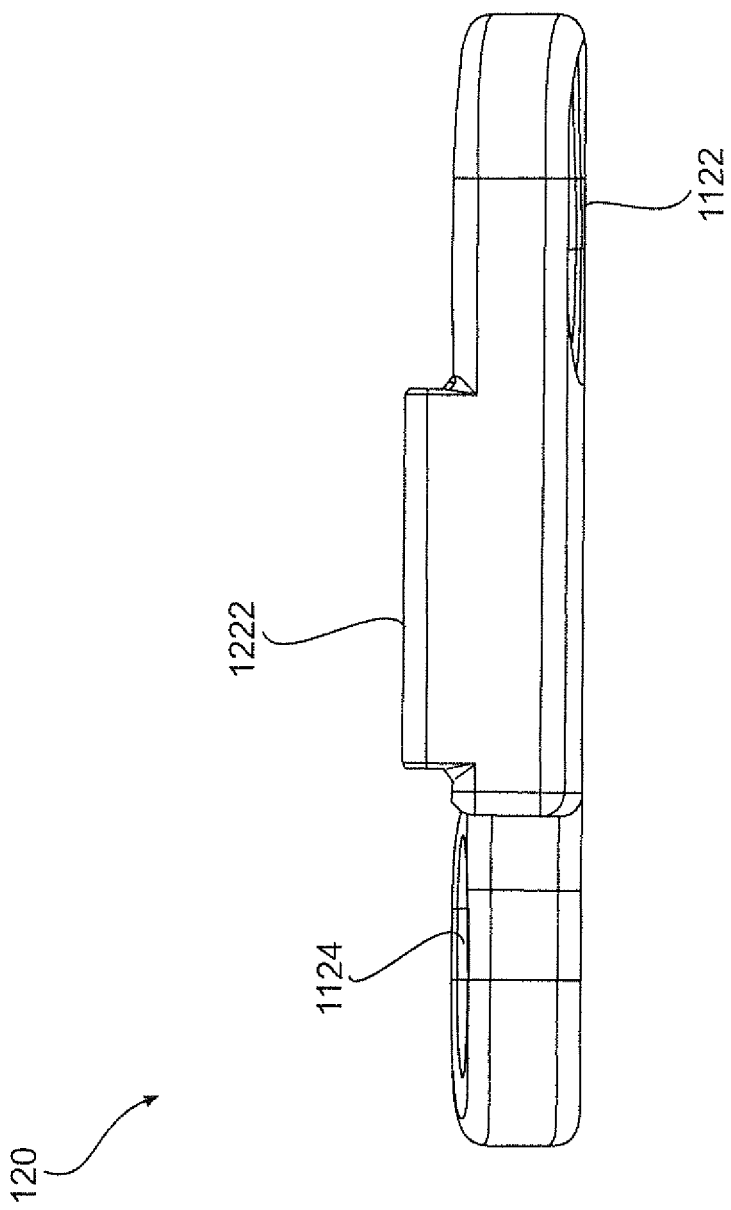
FIG. 13 illustrates a side view of the exemplary bone plate.
Figure 14:
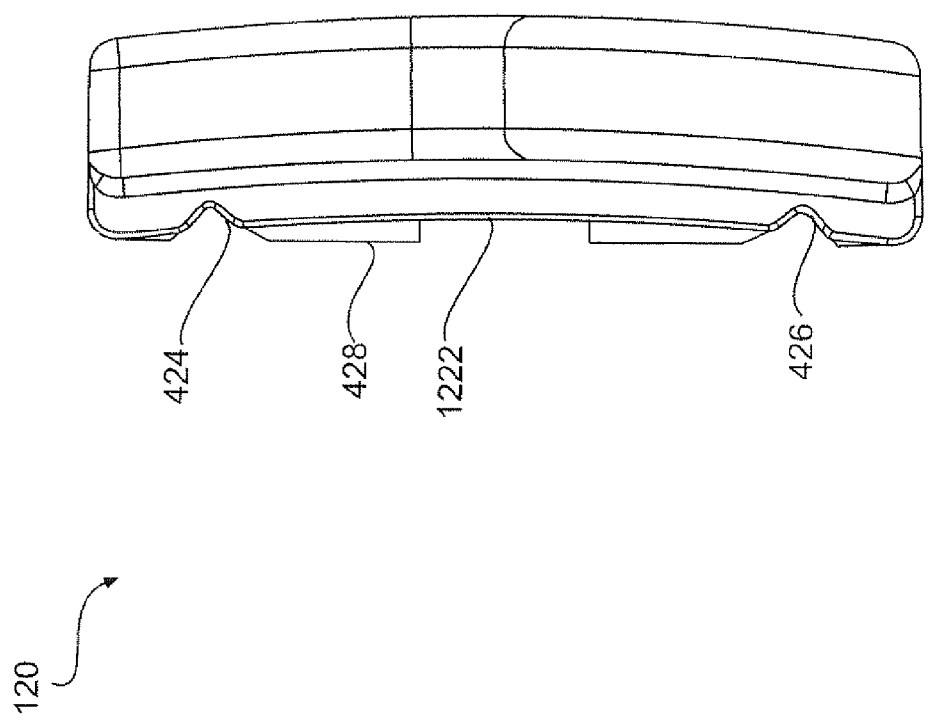
FIG. 14 illustrates a top view of the exemplary bone plate.

As can be seen in FIG. 11, the bone plate 120 may be shaped such that multiple similar bone plates may be used in multi-level fusions. As shown, the two screw holes 1122, 1124 may each be disposed within a respective prominence off of the main plate body. The top prominence may be offset to the right, while the bottom prominence may be offset to the left. As such, the bottom prominence of a similar bone plate (not shown) disposed above the bone plate 120 would be located to the left of the top prominence. In this way, multiple plates similar to the illustrated plate 120 may be tessellated or otherwise may fit together to avoid interference with each other. Various other shapes and structures for avoiding interference between bone plates will be apparent.

Figure 15:
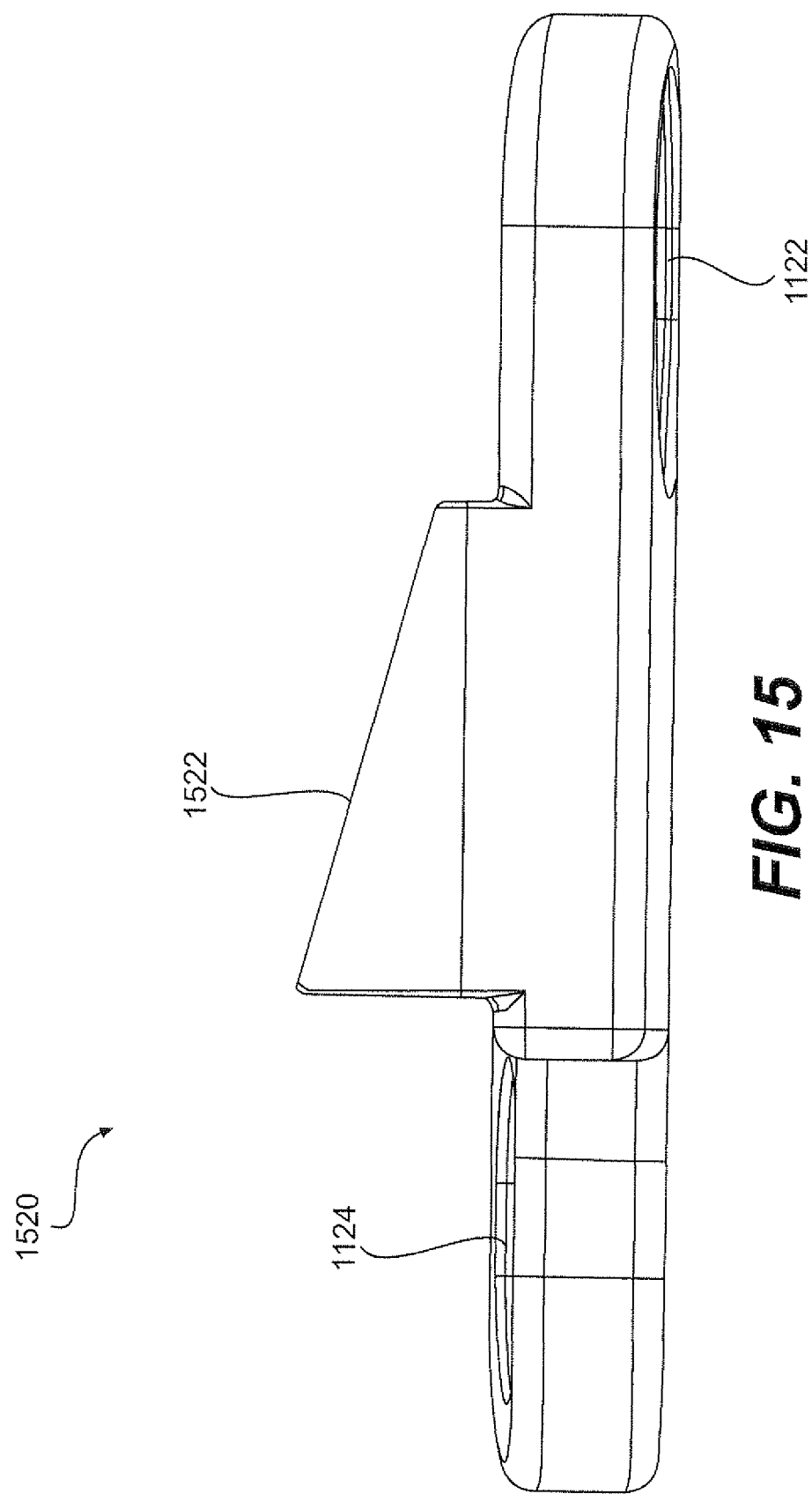
FIG. 15 illustrates a side view of an alternative bone plate including an angled foot.

In various embodiments, the foot of the bone plate may be angled, such that the bone plate, when attached to the cage 110, is oriented at an angle with respect to the cage. As illustrated in FIG. 15, an angled bone plate 1520 may include an angled foot 1522. The angled foot 1522 extends further near the top side of the bone plate than at the bottom side of the bone plate. As will be understood, when attached to a cage 110, the angled bone plate 1520 may be disposed at an angle, such as a 15 degree angle, with respect to the cage 110 due to this alternative wedge-shaped foot structure. In various alternative embodiments, the angled foot (not shown) may additionally or alternatively be at least partially recessed within the bone plate. For example, rather than the end extending further outward near the top side, that end of the angled foot may be recessed within the body of the bone plate. In such embodiments, the opposite end near the bottom side may be flush with the rest of the bone plate, as shown in FIG. 15, or may extend outward from the plate as described with respect to the top side of the angled foot 1522.

It will be understood that various alternative angles may be provided. For example, a wedge-shaped foot may extend further near the left side of the bone plate than the right side of the bone plate. Further, a surgical kit providing an implant according to the present disclosure may provide multiple bone plates having different angled feet (and/or multiple cages having different dimensions), such that the surgeon may select a bone plate having an angle desirable for the procedure at hand. For example, a surgical kit may include a zero-degree bone plate, a two-degree bone plate, a four-degree bone plate, and a six-degree bone plate. Various other angles will be apparent to those of skill in the art.

In various alternative embodiments, rather than being integrated with the bone plate, an angle may be provided by a separate wedge component (not shown). The wedge component may be configured to be disposed between a cage 110 and bone plate 120 to provide a desired angle. In various embodiments, the wedge component may include additional alignment structures configured to, at least partially, engage the cage alignment structure and/or the bone plate alignment structure. In such an embodiment, a kit may be provided with a plurality of wedges having varying angles.

Figure 16:
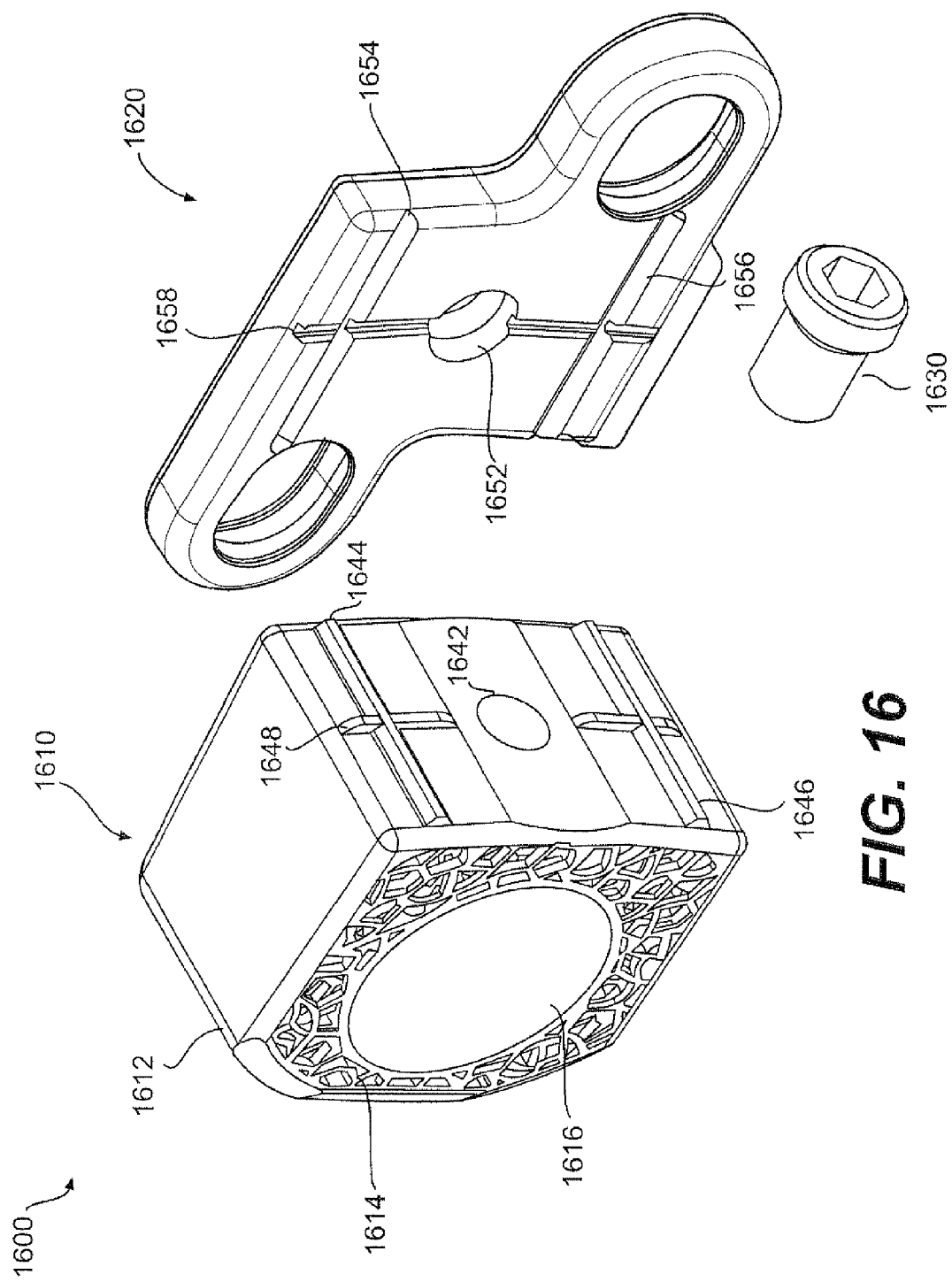
FIG. 16 illustrates a perspective exploded view of an alternative spinal implant.

FIG. 16 illustrates an alternative embodiment of a spinal implant 1600. The alternative spinal implant 1600 may differ from the exemplary spinal implant 100 in a plurality of ways. First, the frame 1612 of the cage 1610 may be shaped differently and may not include any recesses for receiving a cortical margin. Further, the lattice structure 1614 may not be in communication with the through bore because the inner rim 1616 may extend entirely from the top of the cage 1610 to the bottom.

The fastener 1630 may not be threaded and may, instead, be formed of a bio-absorbable material that swells in the presence of water. As such, the fastener hole 1642 of the cage 1610 may not be provided with any threads. Further, the through hole 1652 of the bone plate 1620 may not include an inner ridge to disallow passage of the fastener 1630 head; instead, the through hole 1652 may be sized to accept the head of the fastener 1630 therethrough and may also rely on swelling of the fastener to achieve fixation.

The respective alignment structures of the alternative implant 1600 may also be different from the exemplary implant 100. As can be seen, all three linear features 1644, 1646, 1648 of the cage 1610 may be ridges, while all three linear features 1654, 1656, 1658 of the bone plate 1620 may be grooves. Further, the ridge 1648 may be interrupted near a central, flat surface on the front face of the cage 1610. Various other modifications to the exemplary implant 100 and alternative implant 1600 will be apparent.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be effected while remaining within the spirit and scope of the invention. Accordingly, the foregoing disclosure, description, and figures are for illustrative purposes only and do not in any way limit the invention, which is defined only by the claims.

What is claimed is:

1. A spinal implant for insertion between two vertebrae, the spinal implant comprising:
    a cage sized to be inserted between the two vertebrae, the cage including a cage alignment feature including two parallel ridges and a ridge that intersects the two parallel ridges; and
    a bone plate configured to be attached to the cage and at least one vertebra,
    wherein the bone plate includes a bone plate alignment structure including two parallel grooves intersected by a groove configured to interact with the two parallel ridges and ridge of the cage to provide an indication when the bone plate is properly aligned with the cage.

2. The spinal implant of claim 1, wherein:
    when the bone plate is properly aligned the ridge of the cage is seated within the groove.

3. The spinal implant of claim 1, wherein:
    when the bone plate is properly aligned with the cage comprises the ridge of the cage being seated within the groove of the bone plate.

4. The spinal implant of claim 1, wherein:
    the grooves are linear and the groove that intersects the parallel grooves is perpendicular to the parallel grooves.

5. The spinal implant of claim 1, wherein the bone plate is configured to attach to the cage such that the bone plate is oriented at a non-zero angle with respect to the cage.

6. The spinal implant of claim 5, wherein the bone plate comprises a wedge-shaped foot that contacts the cage.

7. The spinal implant of claim 5, further comprising a wedge configured to be disposed between the cage and the bone plate.

8. A surgical kit comprising:
a cage sized to be inserted between two vertebrae;
a first bone plate configured to be attached to the cage, the first bone plate includes a first wedge having a bone plate alignment structure having linear features, the first wedge having an angled surface relative to the top side of the bone plate to receive the cage such that the bone plate is oriented at a first angle with respect to the cage; and
a second bone plate includes a second wedge having a bone plate alignment structure having linear features, the second wedge configured to be attached to the cage such that the bone plate is oriented at a second angle with respect to the cage,
wherein the first angle does not equal the second angle.

9. The surgical kit of claim 8, wherein:
the cage further includes a cage alignment structure, and
the bone plate alignment structure being configured to interact with the cage comprises
the bone plate alignment structure being configured to interact with the cage alignment structure.

10. The surgical kit of claim 9, wherein:
the bone plate alignment structure comprises at least one of: a bone plate groove and a bone plate ridge;
the cage alignment structure comprises at least one of: a cage groove and a cage ridge; and
the indication when the bone plate is properly aligned with the cage comprises at least one of:
the bone plate ridge being seated within the cage groove, and
the cage ridge being seated within the bone plate groove.

11. The surgical kit of claim 8, wherein:
the bone plate alignment structure includes a first linear feature and a second linear feature perpendicular to the first linear feature;
the first linear feature comprises at least one of: a first groove and a first ridge; and
the second linear feature comprises at least one of: a second groove and a second ridge.

12. An implant comprising:
a cage including a cage alignment feature including two parallel ridges and a third ridge that intersects the two parallel ridges; and
a bone plate configured to be attached to the cage and at least one bone,
wherein the bone plate includes a bone plate alignment structure including two parallel grooves intersected by a groove, configured to interact with the two parallel ridges and the third ridge of the cage to provide an indication when the bone plate is properly aligned with the cage.

13. The implant of claim 12, wherein:
the bone plate alignment structure comprises at least one of: a bone plate groove and a bone plate ridge;
the cage alignment structure comprises at least one of: a cage groove and a cage ridge; and
the indication when the bone plate is properly aligned with the cage comprises at least one of:
the bone plate ridge being seated within the cage groove, and
the cage ridge being seated within the bone plate groove.

14. The implant of claim 12, wherein:
the grooves are linear and the groove that intersects the parallel grooves is perpendicular to the parallel grooves.

15. The implant of claim 12, wherein the bone plate is configured to attach to the cage such that the bone plate is oriented at a non-zero angle with respect to the cage.

16. The implant of claim 15, wherein the bone plate comprises a wedge-shaped foot that contacts the cage.

17. The implant of claim 15, further comprising a wedge configured to be disposed between the cage and the bone plate.

18. A spinal implant for insertion between two adjacent vertebrae, the spinal implant comprising:
a cage comprising:
a frame sized to be inserted between the two vertebrae, the frame comprising a fastener hole and a cage alignment structure, the cage alignment structure comprising two parallel ridges and a ridge that intersects the two parallel ridges
an inner rim surrounding a through bore extending between a top face and a bottom face of the cage;
a bone plate comprising a bone plate alignment structure, a through hole, a first screw hole, and a second screw hole,
wherein the first screw hole and the second screw hole are positioned to overlie the two vertebrae, respectively, when the bone plate is attached to the cage and the cage is inserted between the two vertebrae,
wherein the bone plate alignment structure includes two parallel grooves intersected by a groove and
wherein the bone plate alignment structure and the cage alignment structure are configured to interact with each other to provide an indication when the bone plate is properly aligned with the cage, the indication comprising; the cage ridges being seated within the bone plate grooves and
a fastener operable to attach the bone plate to the cage when the fastener is inserted through the through hole of the bone plate and into the fastener hole of the frame.

* * * * *